(12) United States Patent
Fricke

(10) Patent No.: US 7,007,866 B2
(45) Date of Patent: Mar. 7, 2006

(54) METERING DEVICE FOR THE CONVEYANCE OF SMALL SUBSTANCE QUANTITIES

(75) Inventor: Christian Fricke, Berlin (DE)

(73) Assignee: BSH Bosch und Seimens Hausgeraete GmbH, Munich (DE)

( * ) Notice: Subject to any disclaimer, the term of this patent is extended or adjusted under 35 U.S.C. 154(b) by 350 days.

(21) Appl. No.: 10/601,638

(22) Filed: Jun. 23, 2003

(65) Prior Publication Data
US 2004/0026527 A1 Feb. 12, 2004

Related U.S. Application Data

(63) Continuation of application No. PCT/EP01/15201, filed on Dec. 21, 2001.

(30) Foreign Application Priority Data

Dec. 22, 2000 (DE) ................ 100 65 855

(51) Int. Cl.
*A62C 13/62* (2006.01)
(52) U.S. Cl. ............... 239/302; 239/102.1; 239/101; 239/102.2; 397/84
(58) Field of Classification Search ............ 239/34, 239/57, 302, 101, 102.1, 102.2; 347/6, 84, 347/20, 25, 27, 56, 63, 65
See application file for complete search history.

(56) References Cited

U.S. PATENT DOCUMENTS

| | | | | |
|---|---|---|---|---|
| 4,702,418 A | * | 10/1987 | Carter et al. | ................ 239/101 |
| 5,336,062 A | * | 8/1994 | Richter | ................... 417/413.2 |
| 5,899,381 A | | 5/1999 | Gordon et al. | |
| 6,109,889 A | * | 8/2000 | Zengerle et al. | ......... 417/413.2 |
| 6,474,566 B1 | * | 11/2002 | Hirota et al. | ............ 239/102.2 |

FOREIGN PATENT DOCUMENTS

| JP | 02302534 A | 12/1990 |
|---|---|---|
| WO | 94/19609 | 9/1994 |

OTHER PUBLICATIONS

Anders Olsson et al.: "The First Valve-Less Diffuser Gas Pump", *Proceedings IEEE 10th Annual Int. Workshop on Micro Electro Systems*, Jan. 26-30, 1997, pp. 108-113.

* cited by examiner

*Primary Examiner*—Dinh Q. Nguyen
(74) *Attorney, Agent, or Firm*—John T. Winburn; Russell W. Warnock; Craig J. Loest

(57) ABSTRACT

A metering device for the conveyance of small substance quantities out of a reservoir into an application space by a diaphragm micropump that can be used, in particular, for the conveyance of small doses of gases includes the diaphragm micropump conveying an aromatic through a nozzle/diffuser system in fixed doses out of a reservoir first into a pump chamber and subsequently into an application space. As such, by the action of the diaphragm micropump, the volume and pressure of the pump chamber are varied so that aromatic is alternately drawn out of the reservoir into the pump chamber and pressed out of the pump chamber into the application space. In the event of a periodic change in the volume of the pump chamber, a substance located in the reservoir is, thus, conveyed slowly and in predetermined minimal doses into the application space in the course of time.

14 Claims, 2 Drawing Sheets

METERING DEVICE FOR THE CONVEYANCE OF SMALL SUBSTANCE QUANTITIES

CROSS-REFERENCE TO RELATED APPLICATION

This application is a continuation of copending International Application No. PCT/EP01/15201, filed Dec. 21, 2001, which designated the United States and was not published in English.

BACKGROUND OF THE INVENTION

Field of the Invention

The invention relates to a metering device for the conveyance of small substance quantities out of a reservoir into an application space by a diaphragm micropump that can be used, in particular, for the conveyance of small doses of gases (aromas).

In microsystem technology, micropumps are used in many sectors as special actuators. Their use makes it possible to convey minimal quantities of a gas or of a liquid in exactly dimensioned doses. In addition to use in laboratory technology, micropumps are also employed in modern office technology, and, in this context, a large proportion of their use is in ink-jet printers. These micropumps are distinguished by a compact form of construction and high metering accuracy that is achieved by the use of new materials and by the pumping element acting directly on the substances to be conveyed.

The same object of releasing minimal substance quantities is found in aromatization, such as is carried out, for example, during the drying operation in laundry dryers. In addition of aromatics, at the present time, aromatic cloths are used or plastic containers containing the aromatic that distributes the aroma by evaporation are used. In both instances, the discharge of the aroma takes place in a relatively uncontrolled way, either by the choice of a suitable size of the aromatic cloths or by a suitable dimensioning of the orifice cross-section of the containers. Both methods are, therefore, subject to pronounced fluctuations as a function of the temperature. Moreover, their application is not very user-friendly, and an unnecessary amount of consumable material occurs. However, the use of conventional micropumps that do not have the disadvantages just mentioned, has not gained acceptance because the accuracy that these offer is not necessary in aromatization and, therefore, the use of the costly high-precision pumps is not justified. However, because the aromatic essences are very costly, a sparing demand-controlled application is a plainly desirable aim.

SUMMARY OF THE INVENTION

It is accordingly an object of the invention to provide a metering device for the conveyance of small substance quantities that overcomes the hereinafore-mentioned disadvantages of the heretofore-known devices of this general type and that provides an inexpensive device ensuring a metering of minimal substance quantities over long periods of time. At the same time, the invention implements as compact a construction of the device as possible by the avoidance of movable parts, in order, thereby, to reduce waste, maintenance, and costs and to increase the useful life of the device.

With the foregoing and other objects in view, there is provided, in accordance with the invention, a metering device for conveying small quantities of a substance into an application space, including a reservoir for holding the substance to be conveyed, the reservoir having a substance filling level, a diaphragm micropump communicating with the reservoir, a pump chamber disposed between the reservoir and the application space, the pump chamber having a volume varied by activity of the diaphragm micropump, the pump chamber and the reservoir being connected by a first orifice, a second orifice connecting the pump chamber to the application space, the second orifice acting as a nozzle in a direction from the pump chamber towards the application space, and the first orifice acting as a nozzle in a direction from the reservoir to the pump chamber and being disposed above the filling level of the substance in the reservoir for conveying a gaseous component of the substance in the reservoir.

With the objects of the invention in view, there is also provided a metering device for conveying small quantities of a substance into an application space, including a reservoir for holding the substance to be conveyed, the reservoir having a substance filling level above which a gas space is maintained, a diaphragm micropump defining a pump chamber having a volume and being disposed between the reservoir and the application space, the diaphragm micropump varying the volume of the pump chamber, and an orifice assembly defining a first orifice connecting the reservoir to the pump chamber, being a nozzle in a direction from the reservoir to the pump chamber, and being disposed above the filling level for conveying a gaseous component of the substance in the reservoir, and a second orifice connecting the pump chamber to the application space, the second orifice being a nozzle in a direction from the pump chamber to the application space.

Accordingly, a pump chamber is disposed functionally between the reservoir and the application space, the volume of the pump chamber being variable by the activity of the diaphragm micropump. The pump chamber and the reservoir are connected by a first orifice acting as a nozzle in the direction of the pump chamber and the pump chamber and the application space are connected by a second orifice acting as a nozzle in the direction of the application space. The first orifice acting as a nozzle is disposed such that it lies above the filling level of the reservoir.

In accordance with another feature of the invention, the pump chamber and the reservoir have a common boundary surface.

In accordance with a further feature of the invention, the pump chamber and the application space have a common boundary surface.

In accordance with an added feature of the invention, the diaphragm micropump forms a boundary surface of the pump chamber.

In accordance with an additional feature of the invention, the diaphragm micropump forms a boundary surface between the pump chamber and the reservoir.

In accordance with yet another feature of the invention, the diaphragm micropump is a piezoceramic actuator.

In accordance with yet a further feature of the invention, the diaphragm micropump is a bimetal actuator.

In accordance with yet an added feature of the invention, the substance is a liquid.

In accordance with yet an additional feature of the invention, the orifice assembly is a part of the diaphragm micropump.

In accordance with a concomitant feature of the invention, the orifice assembly is integral with the diaphragm micropump.

Other features that are considered as characteristic for the invention are set forth in the appended claims.

Although the invention is illustrated and described herein as embodied in a metering device for the conveyance of small substance quantities, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

DESCRIPTION OF THE PREFERRED EMBODIMENTS

Figure 1:
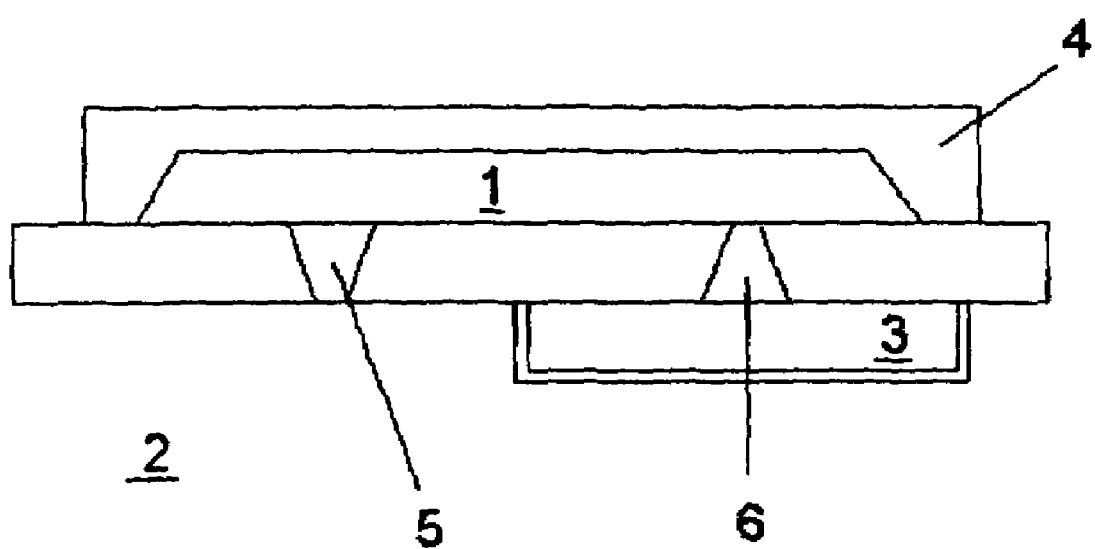
FIG. 1 is a cross-sectional view of the basic construction of the micrometering system according to the invention.

Referring now to the figures of the drawings in detail and first, particularly to FIG. 1 thereof, there is shown a device configured for the distribution of aromatics, for example, for use in laundry dryers. It is composed of a reservoir 3, in which the aromatic is located, the pump chamber 1, one wall of which is formed by a diaphragm micropump 4, and of the nozzle/diffuser system, which connects the pump chamber 1 to the reservoir 3 and to the application space 2. The application space 2 may be an open or a closed space. In the exemplary embodiment described, the reservoir 3 directly adjoins the pump chamber 1. It is separated from the pump chamber 1 by a partition in which an orifice 6 is located. This orifice 6 located in the wall acts as a nozzle in the direction from the reservoir 3 to the pump chamber 1 and as a diffuser in the opposite direction. The pump chamber 1, likewise, directly adjoins the application space 2. A further orifice 5 is located in the wall that separates the application space 2 and the pump chamber 1. In such a case, the further orifice 5 acts as a nozzle in the direction from the pump chamber 1 to the application space 2 and as a diffuser in the opposite direction. By virtue of this special configuration of the nozzle/diffuser system, a pressure difference occurs at the two nozzles during pumping and has the effect that an aromatic located in the reservoir 3 is conveyed into the application space 2.

Figure 2:
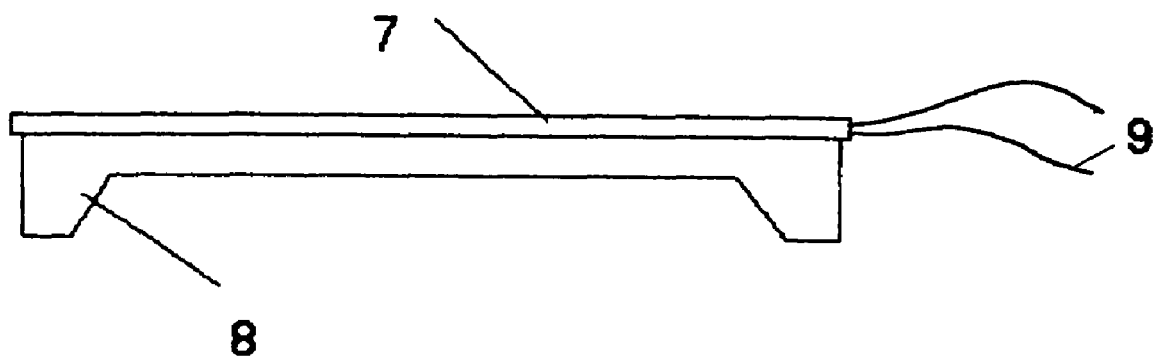
FIG. 2 is a cross-sectional view of the basic construction of a piezoceramic actuator according to the invention.

The diaphragm micropump 4 is formed from a piezoceramic element 7 (FIG. 2) that is attached to a carrier 8 of a rigid material and that, by a voltage being applied (through leads 9, for example), changes its length extent and, thus, acts in a similar way to a bimetal during heating. The curvature that is brought about by the length expansion leads to a reduction or increase in the size of the volume of the pump chamber 1. A bimetal actuator could, therefore, also be used as a diaphragm micropump 4 instead of the piezoceramic element 7 with carrier 8. However, the use of the piezoceramic element 7 affords several advantages. For use in micropumps, above all, the high frequency with which piezoelectric elements can be activated, in conjunction with the expansion behavior that can be controlled extremely accurately by the applied voltage, is of importance.

The device according to the invention conveys an aromatic located in a reservoir 3, through a system having a nozzle and of a diffuser, in fixed doses into an application space 2, using a diaphragm micropump 4. What is achieved, thereby, is that the gaseous component of an aromatic located as liquid in a reservoir 3 is released in small quantities. This is achieved, using a system including a nozzle (orifice 5) and a diffuser (orifice 6), in combination with a diaphragm micropump 4. The aromatic is located in a reservoir 3 connected through the orifice 6 to a pump chamber 1 that, in turn, is connected to the application space 2. The diaphragm micropump 4 has the effect that the volume and the pressure in the pump chamber 1 change periodically, are reduced or are increased. By an increase in volume, that is to say, a reduction in pressure, part of the aromatic present in gaseous form is sucked through the diffuser (orifice 6), out of the reservoir 3 into the pump chamber 1 because, as a result of the dimensioning of the nozzle (orifice 5) and diffuser (orifice 6), the suction action is greater at the diffuser 6 than at the nozzle 5. The result of this is that, although substance passes out of the reservoir 3 into the pump chamber 1, scarcely any gas passes out of the application space 2 into the pump chamber 1. When the volume of the pump chamber 1 is subsequently reduced (the pressure is increased), by virtue of the special configuration of the nozzle and of the diffuser, the substance located in the pump chamber 1 passes into the application space 2, but not or only to a lesser extent into the reservoir 3. Thus, in the event of a periodic change in the volume of the pump chamber 1, a substance located in the reservoir 3 is conveyed slowly and in predetermined minimal doses into the application space 2 in the course of time.

One possible area of use of the micrometering system is, for example, in the drying operation in a laundry dryer. The micrometering system may, in such a case, be integrated in the dryer. Because only extremely small quantities of the aromatic are required for each drying operation, a correspondingly small reservoir 3 is sufficient for a long period of time for which the average useful life of the dryer may be assumed as a reference point.

The use of the micrometering system with suitably dimensioned nozzles, together with the reservoir 3, does not involve any movable parts and is, therefore, virtually maintenance-free, small, and cost-effective.

The invention is not restricted to the exemplary embodiment illustrated here. On the contrary, it is possible, by combination and modification of the measures and features, to implement further configuration variants, without departing from the scope of the invention.

I claim:

1. A metering device for conveying small quantities of a liquid substance into an application space, comprising:

a reservoir for holding the liquid substance to be conveyed, said reservoir having a liquid substance filling level above which a gas space is maintained;

a diaphragm micropump communicating with said reservoir;

a pump chamber disposed between said reservoir and the application space, said pump chamber having a volume varied by activity of said diaphragm micropump;

said pump chamber and said reservoir being connected by a first orifice;

a second orifice connecting said pump chamber to the application space, said second orifice acting as a nozzle in a direction from said pump chamber towards the application space; and a gaseous component of the liquid substance located in said reservoir is released in small quantities to said air space above said filling level in said reservoir said first orifice acting as a nozzle in a direction from said reservoir to said pump chamber and being disposed above said filling level of the substance in said reservoir for conveying said gaseous component of the liquid substance from said air space in said reservoir.

2. The metering device according to claim 1, wherein said pump chamber and said reservoir have a common boundary surface.

3. The metering device according to claim 1, wherein said pump chamber and the application space have a common boundary surface.

4. The metering device according to claim 1, wherein said diaphragm micropump forms a boundary surface of said pump chamber.

5. The metering device according to claim 1, wherein said diaphragm micropump forms a boundary surface between said pump chamber and said reservoir.

6. The metering device according to claim 1, wherein said diaphragm micropump is a piezoceramic actuator.

7. The metering device according to claim 1, wherein said diaphragm micropump is a bimetal actuator.

8. A metering device for conveying small quantities of a liquid substance into an application space, comprising:
   a reservoir for holding the liquid substance to be conveyed, said reservoir having a liquid substance filling level above which a gas space is maintained;
   a diaphragm micropump defining a pump chamber having a volume and being disposed between said reservoir and the application space, said diaphragm micropump varying said volume of said pump chamber; and
   an orifice assembly defining:
      a first orifice:
         connecting said reservoir to said pump chamber;
         being a nozzle in a direction from said reservoir to said pump chamber; a gaseous component of the liquid substance located in said reservoir is released in small quantities to said air space above said filling level in said reservoir and
         being disposed above said filling level for conveying said gaseous component of the liquid substance from said air space in said reservoir; and
      a second orifice connecting said pump chamber to the application space, said second orifice being a nozzle in a direction from said pump chamber to the application space.

9. The metering device according to claim 8, wherein said pump chamber and said reservoir have a common boundary surface.

10. The metering device according to claim 8, wherein said pump chamber and the application space have a common boundary surface.

11. The metering device according to claim 8, wherein said orifice assembly is a part of said diaphragm micropump.

12. The metering device according to claim 8, wherein said orifice assembly is integral with said diaphragm micropump.

13. The metering device according to claim 8, wherein said diaphragm micropump is a piezoceramic actuator.

14. The metering device according to claim 8, wherein said diaphragm micropump is a bimetal actuator.

* * * * *

UNITED STATES PATENT AND TRADEMARK OFFICE
CERTIFICATE OF CORRECTION

PATENT NO. : 7,007,866 B2
DATED : March 7, 2006
INVENTOR(S) : Fricke

It is certified that error appears in the above-identified patent and that said Letters Patent is hereby corrected as shown below:

<u>Title page,</u>
Item [73], Assignee, should read -- BSH Bosch und Siemens Hausgeraete GmbH, Munich (DE) --.

Signed and Sealed this

Twenty-fifth Day of April, 2006

JON W. DUDAS
*Director of the United States Patent and Trademark Office*